US00PP17753P2

(12) United States Plant Patent
Hofmann

(10) Patent No.: US PP17,753 P2
(45) Date of Patent: May 22, 2007

(54) **NEW GUINEA *IMPATIENS* PLANT NAMED 'FISNICS PURPINK'**

(50) Latin Name: *Impatiens hawkeri*
Varietal Denomination: Fisnics Purpink

(75) Inventor: Birgit Christa Hofmann, Bendorf (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 11/330,837

(22) Filed: Jan. 12, 2006

(51) Int. Cl.
*A01H 5/00* (2006.01)

(52) U.S. Cl. ..... Plt./318

(58) Field of Classification Search ..... Plt./318
See application file for complete search history.

*Primary Examiner*—Anne Marie Grunberg
*Assistant Examiner*—Georgia Helmer
(74) *Attorney, Agent, or Firm*—Jondle & Associates P.C.

(57) ABSTRACT

A new New Guinea *Impatiens* plant particularly distinguished by large, round to butterfly-shaped brilliant red-purple flowers that are well above the foliage, early to medium flowering, deep green, elliptically shaped foliage, and a medium plant habit that is round, bushy and moderately tight, is disclosed.

1 Drawing Sheet

Genus and species: *Impatiens hawkeri* W. Bull.
Variety denomination: 'Fisnics Purpink'.

BACKGROUND OF THE NEW PLANT

The present invention comprises a new and distinct cultivar of New Guinea *Impatiens,* botanically known as *Impatiens hawkeri* W. Bull, and hereinafter referred to by the cultivar name 'Fisnics Purpink'. The new cultivar originated from a hybridization made in the year 2000 in Hillscheid, Germany. The female parent was the proprietary New Guinea *Impatiens* plant 'K99-5424-1' (unpatented), while the male parent was the commercial New Guinea *Impatiens* plant 'Fisupnic Hot Pink' (U.S. Plant patent application Ser. No. 10/829,215). The seeds produced by the hybridization were sown in Galdar, Gran Canaria, Spain in the late Fall of 2000. A single plant selection was chosen for further evaluation and for asexual propagation in April 2001 in Galdar, Gran Canaria, Spain.

The new cultivar was created in 2001 in Hillscheid, Germany and has been asexually reproduced repeatedly by vegetative cuttings and tissue culture in Galdar, Gran Canaria, Spain and Hillscheid, Germany over a three-year period. 'Fisnics Purpink' has not been observed under all possible environmental conditions. The present invention has been found to retain its distinctive characteristics through successive asexual propagations.

Plant Breeder's Rights for this cultivar were applied for in Switzerland on Mar. 30, 2005 and in Canada on Apr. 20, 2005.

SUMMARY OF THE INVENTION

The following are the most outstanding and distinguishing characteristics of this new cultivar when grown under normal horticultural practices in Hillscheid, Germany and Langley, British Columbia, Canada.

1. Uniform, brilliant red-purple flowers;
2. Very large, round to butterfly-shaped flowers well above the foliage;

3. Deep green, elliptically shaped foliage;
4. A medium size, round and bushy and only moderately tight plant habit; and
5. An early to medium flowering response.

DESCRIPTION OF PHOTOGRAPH

This new New Guinea *Impatiens* plant is illustrated by the accompanying photograph which shows overall plant habit including blooms, buds, and foliage of the plant; the colors shown are as true as can be reasonably obtained by conventional photographic procedures. The photograph is of a whole plant about 13-weeks old, grown in a greenhouse in Hillscheid, Germany, in late Spring.

DESCRIPTION OF THE NEW CULTIVAR

The following detailed descriptions set forth the distinctive characteristics of 'Fisnics Purpink'. The data which define these characteristics were collected from asexual reproductions carried out in Hillscheid, Germany. The plant history was taken on 11- to 12-week old plants which were planted as rooted cuttings in 12-cm pots in late February 2005, and then grown in a greenhouse at a minimum temperature of 16° C. Color readings were taken under natural light in the greenhouse. Color references are primarily to The R.H.S. Colour Chart of The Royal Horticultural Society of London (R.H.S.) (2001).

DETAILED BOTANICAL DESCRIPTION OF THE NEW PLANT

Classification:
*Family.*—Balsaminaceae.
*Botanical.*—*Impatiens hawkeri* W. Bull.
*Common name.*—New Guinea *Impatiens.*

Parentage:
*Female parent.*—'K99-5424-1' a proprietary purple-pink flowered New Guinea *Impatiens* plant (unpatented).

*Male parent.*—'Fisupnic Hot Pink' a light red-purple flowered New Guinea *Impatiens* plant (U.S. Plant patent application Ser. No. 10/829,215).

Growth:

*Growth and branching habit.*—Medium size, round, bushy, and well-branched; the growth is indeterminate, though weak after the beginning of flowering.

*Height.*—13.8 cm.

*Width.*—22.8 cm.

*Propagation.*—Terminal tips for cuttings.

*Time to produce a finished flowering plant.*—9 to 10 weeks for a 12-cm pot.

*Time to initiate and develop roots.*—18 days at 22° C.

Branches:

*Average number.*—5.9.

*Length of branches.*—12 cm to 14 cm.

*Internode length.*—4.0 cm to 6.0 cm.

*Diameter of branches.*—0.7 cm to 0.8 cm.

*Stem color.*—RHS 185A (purple brown) at mid point, RHS 187B at tips.

Leaves:

*Arrangement.*—Primarily in whorls.

*Size.*—Length: 11.3 cm. Width: 4.5 cm.

*Shape.*—Elliptic.

*Margin.*—Slightly serrate, ciliated.

*Apex.*—Acuminate.

*Base.*—Acute.

*Color* (*mature leaves*).—Upper surface: near RHS 139A (deep-green). Lower surface: RHS 138B (light-green).

*Color* (*immature leaves*).—Upper surface: near RHS 143A. Lower surface: RHS 138B (light-green).

*Texture.*—Surface is glossy, glabrous, smooth or faintly rippled.

*Venation color.*—Upper surface: RHS 53C (reddish) mainly at the leaf base. Lower surface: RHS 53A (deep-red).

*Variegation.*—None.

*Petioles.*—Length: 1.0 cm. Diameter: 0.3 cm to 0.4 cm. Color: Upper surface: RHS 185A (deep reddish-purple). Lower surface: RHS 187C (dark purple). Texture: Glabrous.

Flower buds:

*Shape.*—Ovoid.

*Size.*—Length: 2.3 cm. Diameter: 1.6 cm.

*Color.*—RHS N57B.

Inflorescence:

*Blooming habit.*—9 to 10 weeks after planting of rooted cuttings.

*Inflorescence type.*—Flowers appear solitary in the leaf axils of the upper nodes of the stems.

*Number of flowers per node.*—5 to 7, in various stages of development.

*Flowering season.*—Indeterminate, continuously, mainly from March to October, depending on light intensity.

*Lastingness of individual blooms.*—Up to 12 days (in a greenhouse at about 18° C.).

*Peduncle.*—Color: RHS 185A (brownish-purple). Size: Length: 5.5 cm to 6.0 cm. Diameter: 0.15 cm. Texture: Glabrous, flexible.

Flowers:

*Form of corolla.*—Single-type, 5 petals.

*Shape of corolla.*—Nearly round with the petals overlapping, weak butterfly shape with the lateral petals somewhat upward directed.

*Corolla size.*—Length: 8.7 cm. Width: 8.1 cm. Depth: 1.2 cm.

Petals:

*Shape.*—Cordate, somewhat lobed at the top.

*Apex.*—Emarginate.

*Base.*—Attenuate.

*Margin.*—Entire.

*Petal size.*—Top: Length: 3.7 cm. Width: 5.3 cm. Lateral: Length: 3.5 cm to 3.7 cm. Width: 4.5 cm to 4.6 cm. Lower: Length: 3.8 cm. Width: 5.0 cm to 5.2 cm.

*Color.*—Upper surface: RHS N66B, no markings. Lower surface: Deeper than RHS 58B. Eye Zone: No distinct eye zone.

*Petal texture.*—Smooth, silky.

*Aspect.*—Flat or weakly slanting upward, the banner petal may be slightly cupped.

Spur:

*Shape.*—Downwardly curved.

*Color.*—RHS 53B (dull red).

*Size.*—Length: 4.5 cm to 5.0 cm. Diameter: 0.3 cm (at the flower end).

Reproductive organs:

*Stamens.*—Number: 5 fused. Stamen color (upper surface color): RHS 46C (light-red). Anthers: Fused, hooded. Pollen color: RHS 8D (whitish-yellow).

*Pistils.*—Style and stigma: 5, very short, RHS 150D (pale-yellow). Ovary: 5-celled. Ovary length: 0.5 cm. Ovary color: RHS 147A (surface green to dark green).

Fruit and seed set: No seed set observed.

Disease and insect resistance: No particular resistance or susceptibility has been observed.

COMPARISON WITH PARENTAL AND COMMERCIAL CULTIVARS

'Fisnics Purpink' differs from the female parent 'K99-5424-1' (unpatented) by having larger deeper-purple flowers and medium green foliage, while 'K99-5424-1' has purple-pink flowers and dark-green foliage with red veins.

'Fisnics Purpink' differs from the male parent 'Fisupnic Hot Pink' (U.S. Plant patent application Ser. No. 10/829, 215), by having deeper purple colored flowers, slightly deeper green foliage and a medium-sized plant habit, while 'Fisupnic Hot Pink' is tall.

'Fisnics Purpink' differs from the commercial cultivar 'Fisnics Purple' (U.S. Plant Pat. No. 14,728) by having larger flowers of a more reddish, less bluish hue than 'Fisnics Purple'. Additionally, 'Fisnics Purpink' has a less compact plant habit and taller canopy than 'Fisnics Purple'.

'Fisnics Purpink' differs from cultivar 'Fisnics Purdeep' (U.S. Plant Patent applied for) by having a brighter and more reddish flower color, lighter green foliage color and shorter leaves than 'Fisnics Purdeep'.

I claim:

1. A new and distinct cultivar of New Guinea *Impatiens* plant as shown and described herein.

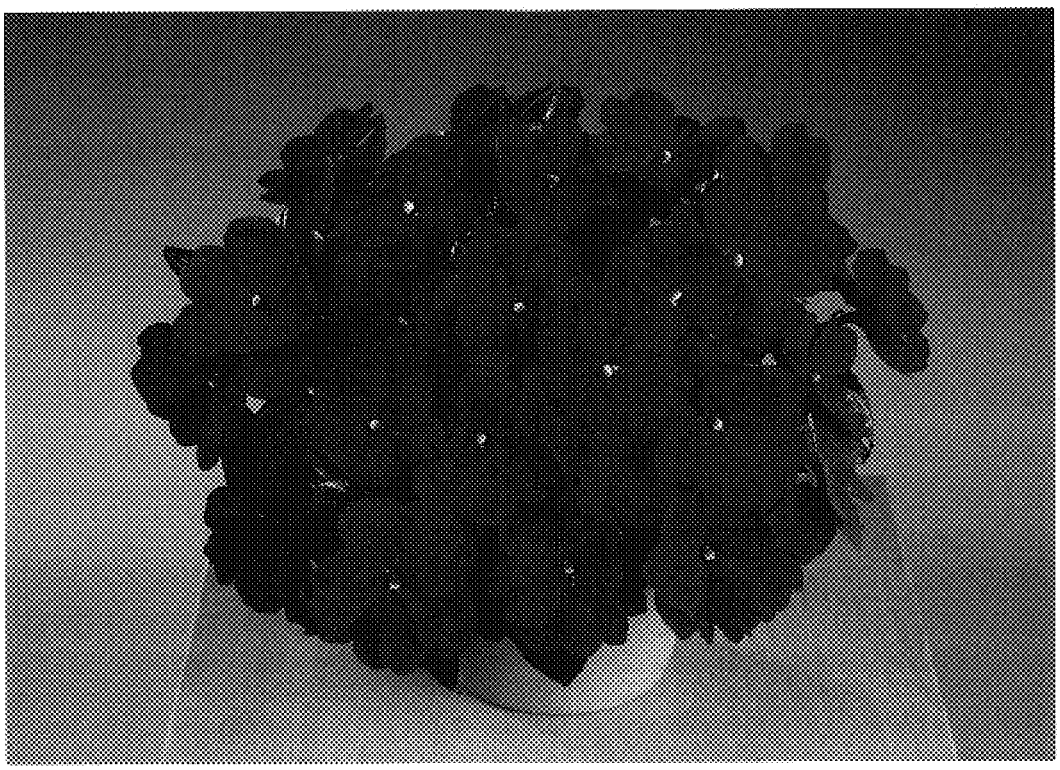

* * * * *